United States Patent [19]
Sarto et al.

[11] Patent Number: 6,022,689
[45] Date of Patent: *Feb. 8, 2000

[54] SITU HYBRIDIZATION SLIDE PROCESSES

[75] Inventors: Gloria E. Sarto; Donald M. Thompson, both of Albuquerque, N.Mex.

[73] Assignee: University of New Mexico, Albuquerque, N.Mex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/727,951

[22] Filed: Oct. 9, 1996

Related U.S. Application Data

[63] Continuation-in-part of application No. 08/418,704, Apr. 7, 1995, Pat. No. 5,750,340.

[51] Int. Cl.$^7$ .................................................. C12Q 1/68

[52] U.S. Cl. ................................................................ 435/6

[58] Field of Search ............................ 435/5, 6; 422/104

[56] References Cited

U.S. PATENT DOCUMENTS

| | | | |
|---|---|---|---|
| 4,302,204 | 11/1981 | Wahl et al. ............................ | 23/230.3 |
| 4,358,535 | 11/1982 | Falkow et al. ............................. | 435/5 |
| 4,647,529 | 3/1987 | Rodland et al. ............................ | 435/6 |
| 4,689,294 | 8/1987 | Boguslawski et al. ..................... | 435/6 |
| 4,886,741 | 12/1989 | Schwartz ................................... | 435/5 |
| 4,888,278 | 12/1989 | Singer et al. ............................... | 435/6 |
| 5,132,207 | 7/1992 | Kohne et al. ............................... | 435/6 |
| 5,225,326 | 7/1993 | Bresser et al. .............................. | 435/6 |
| 5,232,831 | 8/1993 | Milliman et al. ........................... | 435/6 |
| 5,316,906 | 5/1994 | Haugland et al. ......................... | 435/4 |
| 5,447,841 | 9/1995 | Gray et al. ................................. | 435/6 |
| 5,506,098 | 4/1996 | Zarling et al. .............................. | 435/6 |
| 5,512,436 | 4/1996 | Stone ......................................... | 435/6 |
| 5,521,061 | 5/1996 | Bresser et al. .............................. | 435/5 |
| 5,527,510 | 6/1996 | Atwood et al. ........................ | 422/104 |
| 5,719,023 | 2/1998 | Zarling et al. .............................. | 435/6 |
| 5,750,340 | 5/1998 | Kim et al. .................................. | 435/6 |
| B1 4,358,535 | 5/1956 | Falkow et al. .............................. | 435/5 |

FOREIGN PATENT DOCUMENTS

| | | | |
|---|---|---|---|
| WO 90/02204 | 8/1990 | WIPO .............................. | C12Q 1/68 |
| WO 95/03431 | 2/1995 | WIPO .............................. | C12Q 1/68 |

OTHER PUBLICATIONS

Kawaguchi et al. Mol. and Cell. Probes 6: 349–352 Aug. 1992.

Griffin, D., "Fluorescent in Situ Hybridization for the Diagnosis of Genetic Disease at Postnatal, Prenatal, and Pre-implementation Stages," *International Review of Cytology*, vol. 153, pp. 1–35 (1994).

Haar, F.M., et al., "A Rapid FISH Technique for Quantitative Microscopy," *Biotehniques Research Reports*, vol. 17, pp. 346–353 (1994).

Klinger, K., et al. "Rapid Detection of Chromosome aneuploidies in Uncultured Amniocytes by Using Fluorescence in Situ Hybridization (FISH)," Am.Human Genet., vol. 51, pp. 55–65 (1992).

Kuo, W.L., et al., "Detection of Aneuploidy Involving Chromosomes 13, 18 or 21, by Fluorescence in SItu Hybridization (FISH) to Interphase and Metaphase Amniocytes," Am. J. Hum. Genet., vol. 49, pp. 112–119 (1991).

Ward, B., et al., "Rapid Prenatal Diagnosis of Chromosomal Aneuploidies by Fluorescence In Situ Hybridization: Clinical Experience with 4,500 Specimens," Am. J. Hum. Genet., vol. 52, pp. 854–865 (1993).

Yang, T.T., et al., "Fast Hybridization Solution for the Detection of Immobilized Nucleic Acids," Biotechniques Research Reports, vol. 18, No. 3, pp. 498–503 (1995).

Visakorpi, Tapio, et al., "Sensitive Detection of Chromosome Copy Number Aberrations in Prostate Cancer by Fluorescence In Situ Hybridization," Am. J. Pathology, vol. 145, No. 3, pp. 624–630 (Sep. 1994).

Chang, Henry,"In Situ Transcription with Tth DNA Polymerase and Fluorescent Nucleotides," J. Immunol. Methods, vol. 176, pp. 235–243 (1994).

Florijn, R.J., et al., "Analysis of Antifading Reagents for Fluorecence Microscopy," Cytometry, vol. 19, pp. 177–182 (1995).

Hyytinen, Eija, et al., "Improved Technique for Analysis of Formalin–Fixed, Paraffin–Embedded Tumors by Fluorescence In Situ Hybridization," Cytometry, vol. 16, pp. 93–993 (1994).

Clonetech Laboratories, Inc.: "Express Hybridization Solution," (PT1190–1) Catalog #8015–1, Product Protocol Cover Sheet and pp. 5,7,9 and 11.

Material Safety Data Sheet, "Formamide," Fisher Scientific, Inc., pp. 1–4 (1995).

Maniatis, T., et al., *Molecular Cloning –A Laboratory Manual*, "Extraction, Purification and Analysis of mRNA for Eukaryotic Cells," Cold Spring Harbor Laboratory, pp. 188–190 (1982).

Brochure: Oncor Detection Kit: Rapid Chromosome in Situ Hybridization System (Rapid Hybridization Protocol for Direct–Labeled (FITC or Texas Red) Satellite DNA Probes), Oncor, Inc., pp. 1–13, (1993).

Pamphlet: CyProbe (Chromosome Detection Sequences) Cat. No. A6300X (Biological Detection Systems, Inc.).

Pamphlet: Imagentics Spectrum CEP Direct Chromosomes Enumeration System (Procedural Kit), Imagentics Inc..

*Primary Examiner*—Kenneth R. Horlick
*Attorney, Agent, or Firm*—Deborah A. Peacock; Jeffrey D. Myers; D. Goelet Kehl

[57] ABSTRACT

A method of preparing flourescent in situ hybridization slides, comprising: providing a slide with a raised ring thereon; providing to the slide a DNA probe; providing to the slide cells and target DNA; providing to the slide a formamide-free mixture of 10%±2% by weight dextran sulfate and 15%–25% glycerol and 0.9% by weight salt or a solution of 10%±2% by weight dextran sulfate, 10–30% by volume formamide and 0.9% by weight salt; placing a coverglass on the ring; denaturing and hybridizing the slide; and performing a post-hybridization wash of the slide.

55 Claims, 7 Drawing Sheets

SITU HYBRIDIZATION SLIDE PROCESSES

CROSS-REFERENCE TO RELATED APPLICATIONS

This application is a continuation-in-part application of U.S. patent application Ser. No. 08/418,704, entitled "In Situ Hybridization Solution and Process", to Kim et al., filed on Apr. 7, 1995, U.S. Pat. No. 5,750,340, the teachings of which are incorporated herein by reference.

BACKGROUND OF THE INVENTION

1. Field of the Invention

This invention relates to fluorescence in situ hybridization.

2. Background Art

In situ hybridization (ISH) is a powerful and versatile tool for the detection and localization of nucleic acids (DNA and RNA) within cell or tissue preparations. By the use of labeled DNA or anti-sense RNA probes, the technique provides a high degree of spatial information in locating specific DNA or RNA sequences within individual cells or chromosomes. ISH is widely used for research and potentially for diagnosis in the areas of prenatal genetic disorders, and molecular cytogenetics. In the general area of molecular biology, ISH is used to detect gene expression and over-expression, to map genes, to identify sites of gene expression, to localize target genes, and to identify and to localize various viral and microbial infections. Currently, the application of the ISH technology research is being expanded into tumor diagnosis, preimplantation genetic diagnosis for in vitro fertilization, evaluation of bone marrow transplantation, and analysis of chromosome aneuploidy in interphase and metaphase nuclei.

In ISH, labeled nucleic acids (DNA or anti-sense RNA) are hybridized to chromosomes or mRNAs in cells which are immobilized on microscope glass slides (*In Situ Hybridization: Medical Applications* (eds. G. R. Coulton and J. de Belleroche), Kluwer Academic Publishers, Boston (1992); *In Situ Hybridization: In Neurobiology; Advances in Methodology* (eds. J. H. Eberwine, K. L. Valentino, and J. D. Barchas), Oxford University Press Inc., England (1994); and *In Situ Hybridization: A Practical Approach* (ed. D. G. Wilkinson), Oxford University Press Inc., England (1992)). Numerous non-isotopic systems have been developed to visualize labeled DNA probes including; a) fluorescence-based direct detection methods, b) the use of digoxigenin- and biotin-labeled DNA probes coupled with fluorescence detection methods, and c) the use of digoxigenin-and biotin- labeled DNA probes coupled with antibody-enzyme detection methods. When fluorescence-labeled nucleic acid (DNA or RNA) probes are hybridized to cellular DNA or RNA, the hybridized probes can be viewed directly using a fluorescence microscope. By using multiple nucleic acid probes with different fluorescence colors, simultaneous multicolored analysis (i.e., for multiple genes or RNAs) can be performed in a single step on a single target cell. Fluorochrome-directly-labeled nucleic acid probes eliminate the need for multi-layer detection procedures (e.g., antibody-based-systems), which allows fast processing and also reduces non-specific background signals. Therefore, fluorescence in situ hybridization (FISH) has become an increasingly popular and valuable tool in both basic and clinical sciences.

Because of the importance of FISH technology in molecular biology and cytogenetics, optimizing current FISH technology to improve the sensitivity of hybridization (fluorescence) signals, to simplify and thus decrease the time for the process, and to substitute toxic reagents with non-health-hazard chemicals used in the FISH process is desirable. FISH technology for DNA (or RNA) chromosomes is dependent on four major factors: (a) optimal temperature for effective denaturation of double-strand DNAs (separation of two DNA strands); (b) optimal temperature for annealing or hybridization between target DNA (or RNA) and labeled DNA or RNA probes (i.e., DNA or anti-sense RNA fragments with which enzymes, fluorochromes, chromophores, chemiluminescers, bioluminescers, radioisotopes, biotin or avidin are conjugated); (c) selection of suitable solutions to enhance both the denaturation and the hybridization processes; and (d) effective post-hybridization washing conditions. It is essential that the structural integrity of nuclei, chromosomes, cells, tissue sections and spatial resolution of the fluorescence signals not be compromised during the FISH process. Therefore, optimization of FISH technology should include increased hybridization efficiency, increased detection sensitivity, and preservation of cellular, tissue, nuclear, and chromosomal morphology.

Currently, FISH procedures performed by many laboratories around the world are generally very similar to those of Kuo, et al., ("Detection of Aneuploidy Involving Chromosomes 13, 18 or 21, by Fluorescence in Situ Hybridization to Interphase and Metaphase Amniocytes," *Am. J. Hum. Genet.* 49:112–119 (1991)); Klinger, et al., ("Rapid Detection of Chromosome Aneuploidies in Uncultured Amniocytes by Using Fluorescence in Situ Hybridization (FISH)," *Am J. Hum. Genet.* 51:55–65 (1992)); and Ward, B. E., et al., ("Rapid Prenatal Diagnosis of Chromosomal Aneuploidies by Fluorescence in Situ Hybridization; Clinical Experience with 4,500 Specimens," *Am. J. Hum. Genet.* 52:854–865 (1993)). However, most laboratories rely, for convenience on kits available from two major commercial sources: Oncor, Inc., "Rapid Chromosome In Situ Hybridization System", Edition 1, October 1993; and Vysis, Inc. Biological Detection Systems/Amersham, Inc., provides only labeled DNA probes with a recommended FISH protocol (Biological Detection Systems, Inc., 955 William Pitt Way, Pittsburgh, Pa. 15238). All of these FISH procedures are time consuming, labor intensive, extremely tedious, and of very limited detection sensitivity. U.S. Pat. No. 5,225,326, to Bresser, et al., teaches "one step in situ hybridization," wherein both fixation and FISH can purportedly be performed in 5 minutes to 4 hours. Haar, et al., "A Rapid FISH Technique for Quantitative Microscopy," *Bio Techniques*, Vol. 17, No. 2, pp. 346–353 (August 1994), discloses a technique which can "in principle" reduce the time necessary for FISH to thirty minutes.

Scoring fluorescence signals using the FISH procedures described above generally requires a 100× oil-immersion objective lens with a triple bandpass filter due to lower signal sensitivity. The use of a high concentration of formamide during the FISH process appears to incur morphological destruction of cellular, nuclear or chromosomal structure. Furthermore, all of these processes involve the use of formamide during hybridization or the post-hybridization process. Formamide is an expensive, toxic solvent and also a teratogen. Therefore, a formamide-free FISH process is environmentally and hygienically desirable.

SUMMARY OF THE INVENTION

The present invention improves upon that disclosed in U.S. patent application Ser. No. 08/418,704, U.S. Pat. No. 5,750,340. A rapid, simple, and highly sensitive fluorescence in situ hybridization (FISH) procedure was developed on the basis of two preferred denaturation-hybridization solutions: 1) with formamide, 10% dextran sulfate/20% formamide/ 0.9% NaCl or KCl solution; and 2) formamide-free, 10% dextran sulfate/20% glycerol/0.9% NaCl or KCl solution. Labeled nucleic acid (DNA or anti-sense RNA) probes were dissolved in one of these two denaturation-hybridization solutions. The solution containing the labeled probes was applied to nuclei or appropriately treated cells and tissue sections which were immobilized on microscopic glass slides and then glass coverslips were gently placed to allow uniform spreading of the probe solution.

Labeled nucleic acid probes and nucleic acids in chromosomes and appropriately treated cells and tissue sections on the glass slides were simultaneously denatured for approximately 1.5±0.5 minutes in an oven of approximately 100° C.±5° C. with or without a sealant between the coverslip and the glass slide, and then immediately hybridized in an oven at a temperature of approximately 55° C.±5° C. for 5 minutes.

After removing the coverslips from the slides, the hybridized slides were washed in 50% formamide in 0.45% NaCl for 3 minutes at 38° C., and then for 5 minutes in 0.9% NaCl at 38° C. Alternatively, the hybridized slides were washed in formamide-free 0.1–0.2% NaCl at 60° C. for 5 minutes and then for another 3 minutes in new 0.1–0.2% NaCl at 60° C.

After air-drying, slides were counterstained with 4,6-diamidino-2-phenylindole (DAPI) or propidium iodide (PI) solution. Fluorescence signals were visualized with a fluorescence microscope which was equipped with a triple band-pass filter and a 20× or 40× dry objective lens. The whole FISH process took from 5 minutes to 15 minutes. Advantages of these procedures which are based on these two denaturation-hybridization solutions are: 1) elimination of the step of sealing coverslip to slide with rubber cement during the entire FISH process; 2) simplification of FISH processing steps by co-denaturation (an ability to vary the temperatures ±/−10 degrees without negatively affecting the outcome); 3) a rapid FISH process in 15 minutes or less; 4) highly increased sensitivity of hybridization (fluorescence) signals; and 5) development of an entirely formamide-free fluorescence in situ hybridization process. In addition, this process can be used for other non-fluorescence in situ hybridization processes.

The primary objective of this invention is to provide three methods of utilizing non-coated and DNA-coated slides which shorten the time for the fluorescence in-situ hybridization (FISH) process to less than two minutes without compromising cost, efficiency, or signal detection. This invention utilizes the solutions, range of temperatures for denaturation and hybridization and some of the post-hybridization washing conditions denoted in U.S. patent application Ser. No. 08/418,704.

Other objects, advantages and novel features, and further scope of applicability of the present invention will be set forth in part in the detailed description to follow, and in part will become apparent to those skilled in the art upon examination of the following, or may be learned by practice of the invention.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENT (BEST MODE FOR CARRYING OUT THE INVENTION)

The present invention is inclusive of that presented in U.S. patent application Ser. No. 08/418,704, and enhances the described FISH technology in that application. The present invention permits the detection of one copy of target genes or RNA in cultured cells, tissue sections, tumors, and on nitrocellulose or nylon paper for use in association with blotting technology. The present invention permits the detection of a signal in interphase nuclei, using more dilute solutions of the probe than suggested in prior art (Oncor, Inc.; Vysis Inc.; BDS/Amersham, Inc.), thus decreasing the cost of the procedure and increasing the likelihood that screening large populations would be cost effective. The present invention allows the entire procedure to be accomplished at varying temperatures and times, without negatively affecting signal detection, and makes the whole process more forgiving of minor deviations and thus applicable to processing large numbers of samples. The speed and reliability with which FISH can be accomplished with the present invention makes it applicable to those instances where speed is of the essence, e.g., pre-implantation genetics.

Prior art FISH technologies, available from commercial sources, take at least two hours to more than 12 hours. In addition, those procedures involve various laborious steps, separate denaturation of target nucleic acids and labeled probes, separate denaturation and hybridization procedures, and repeated dehydration of target nucleic acids with graded alcohols, etc.

The present invention, in contrast, involves three steps and results in a high detection sensitivity: denaturation; hybridization; and post-hybridization wash. It takes a total of approximately two minutes to perform the FISH process of the present invention. Conventional FISH procedures require precise timing and temperature for the denaturing and hybridization processes. The present invention allows variation in the time and temperature with little effect on the high degree of sensitivity.

Conventional FISH procedures require use of an oil-immersion 100× objective lens for adequate enumeration of signals. In the present invention, because of the optimal composition of the denaturation-hybridization solutions and optimal denaturation-hybridization conditions (temperature and timings), the fluorescence signals become very bright.

Commonly, SSC (saline sodium citrate) is used during the FISH process. With SSC, the pH must be adjusted to around 7.0. Preparation of SSC is a time consuming process. Although SSC may be used instead of the saline with the present invention, in the present invention, SSC may be entirely replaced with saline. There is no need for adjusting the pH of saline for post-hybridization washings, thus shortening and simplifying the FISH process.

The preferred solution is known as solution G (see U.S. patent application Ser. No. 08/418,704), which comprises a formamide-free mixture of 10%±2% by weight dextran sulfate and 15%–25% (preferably 20%) by weight glycerol and 0.9% by weight NaCl, KCl or other salt. A 10%–20% dextran sulfate solution or 20–50% glycerol solution alone, mixed with labeled nucleic acid probes, will not result in effective hybridization. However, the combination of glycerol and dextran sulfate enhances the hybridization remarkably.

An alternative solution, known as solution F (see U.S. patent application Ser. No. 08/418,704), comprises 10%±2% by weight dextran sulfate, 10–30% (preferably 20%) by volume formamide and 0.9% by weight NaCl, KCl or other salt. The formamide is only effective for hybridization in conjunction with the dextran sulfate. Formamide concentrations lower than 15% or higher than 25% can be used for fluorescence in situ hybridization, but the use of these formamide concentrations requires different denaturation temperature settings, different denaturation times. Therefore, the preferred formamide concentration is 20%±5% by volume. In addition, a higher concentration of formamide (above 35%) promotes structural destruction of cellular and nuclear morphology.

Slide Method 1—DNA-coated slide.

With this embodiment of the invention, a defined area of a glass slide is coated with a selected DNA probe. Glass slides with defined areas, e.g., ring(s), are used. A defined area(s) on the slide is coated with specific DNA probes. This can be accomplished by diluting the DNA probe in TE buffer (Tris-EDTA) or other buffers in applying it to the slide and allowing it to dry. The cell sample (target DNA) solution is placed on top of the DNA probe in the previously defined locations and allowed to dry.

Figure 1:
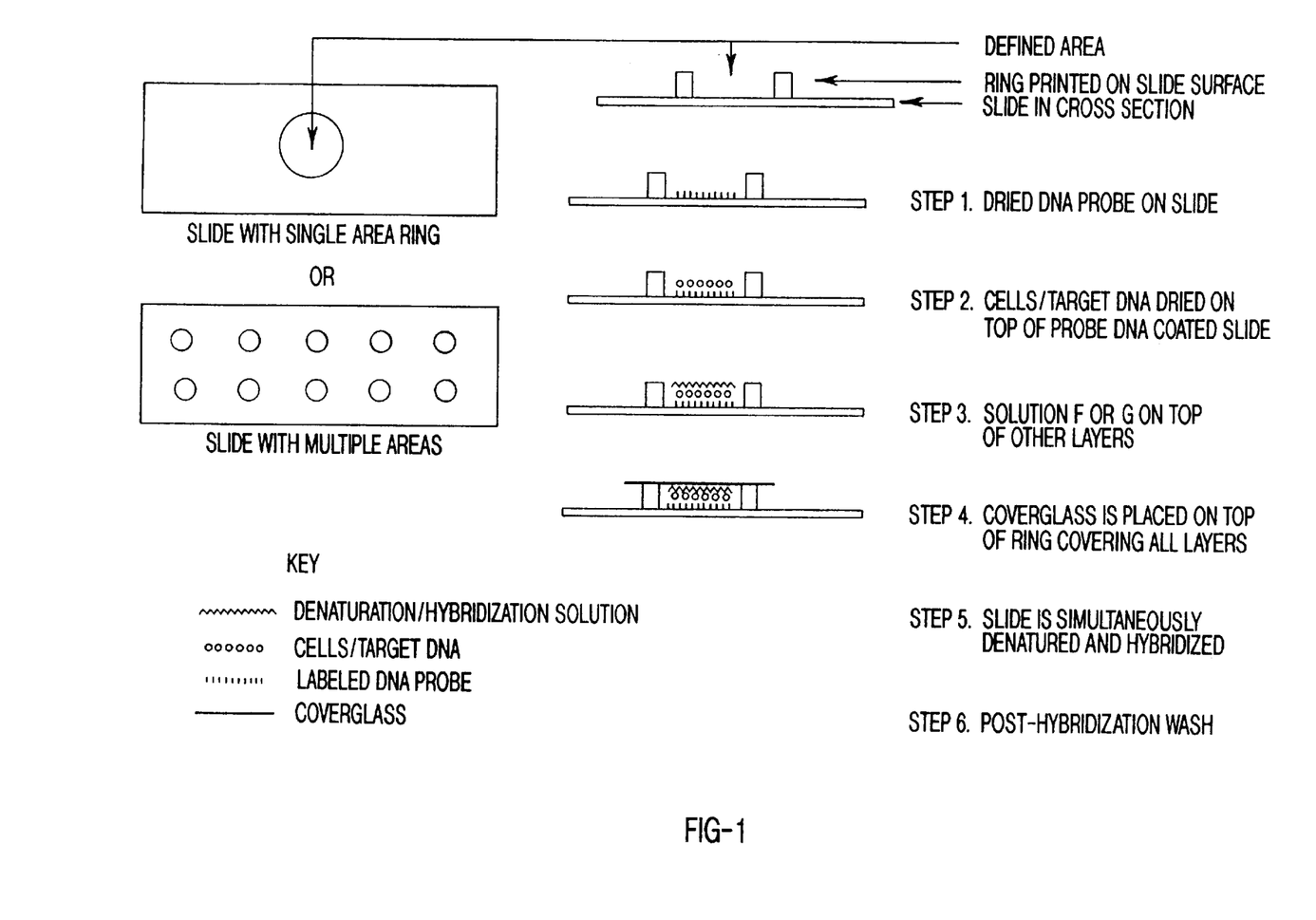
FIG. 1 illustrates a first embodiment of the invention.

One of the previously described solutions, e.g., Solution F or G, is layered over the previously defined area with the dried DNA probe and cell sample (target DNA). A coverglass is placed on top of the defined area and then the dried probe/sample/solution layers on the slide are simultaneously denatured and hybridized. FIG. 1 illustrates this embodiment of the invention.

Slide Methods 2A and 2B.

With these embodiments methods of the invention, the cells (target DNA) are coated with DNA probe.

Slide Method 2A—DNA-coated Cells

Figure 2A:
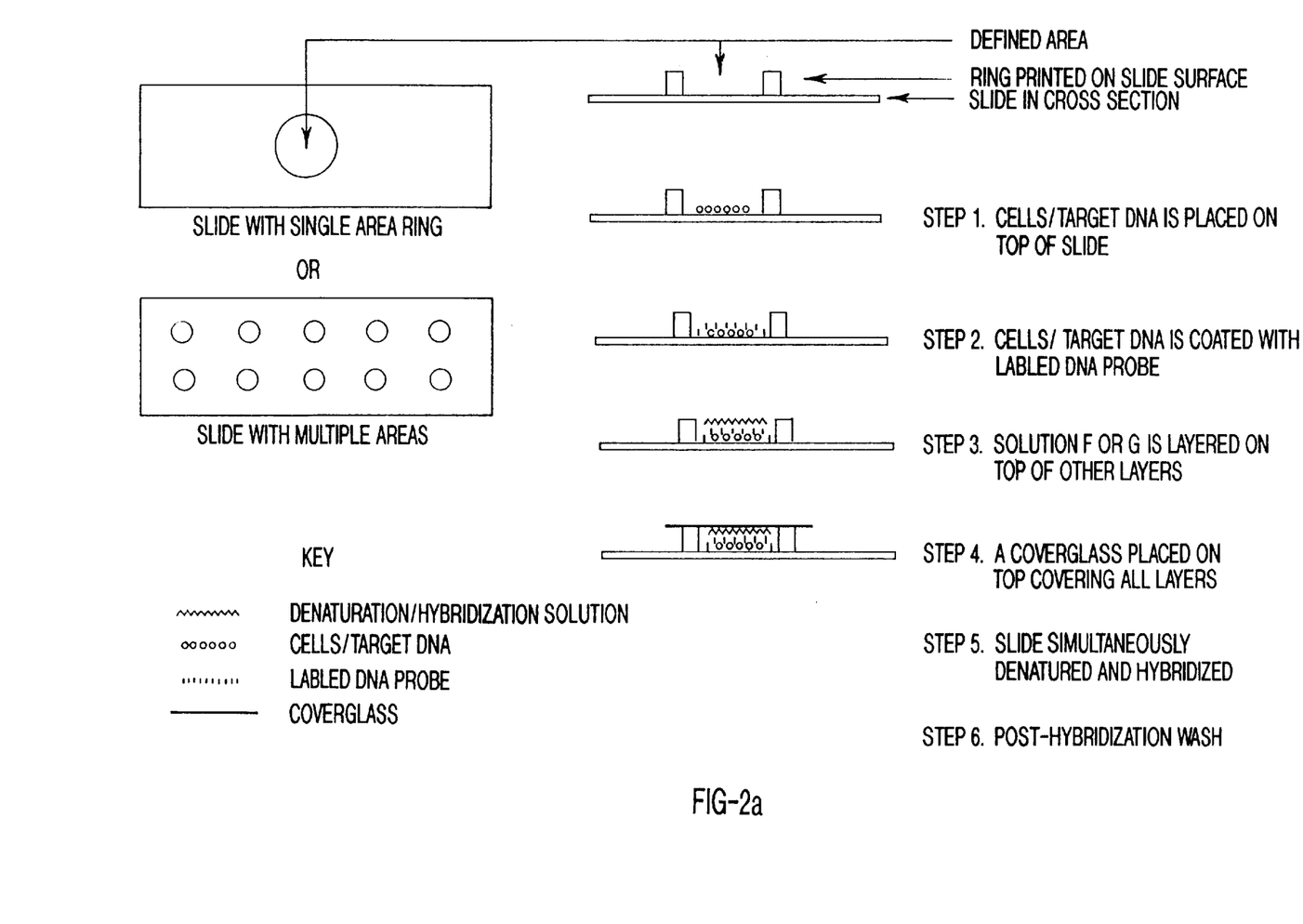
FIG. 2A illustrates a second embodiment of the invention.

Glass slides with defined area(s), e.g., ring(s), are used. The cell sample (target DNA) solution is applied to the slide within a defined area and allowed to dry. The probe DNA in TE or other buffer is applied to the same defined area and is allowed to dry. The cells are coated and thus the DNA is concentrated on the cells. One of a previously described solutions, e.g., Solution F or G, is layered on top of the DNA probe-coated cells. A coverglass is placed over the defined area, and the sample is simultaneously denatured and hybridized. This embodiment of the invention is shown in FIG. 2A.

Slide Method 2B—DNA-coated Cells

An alternative method to slide method 2A is the following: The cell sample solution is centrifuged to pellet the cells. The fluid is decanted. DNA probe in TE buffer or other buffer is applied to the pellet, and the cells are resuspended. The solution of DNA probe and cells is applied to the defined area on the slide and allowed to dry.

Figure 2B:
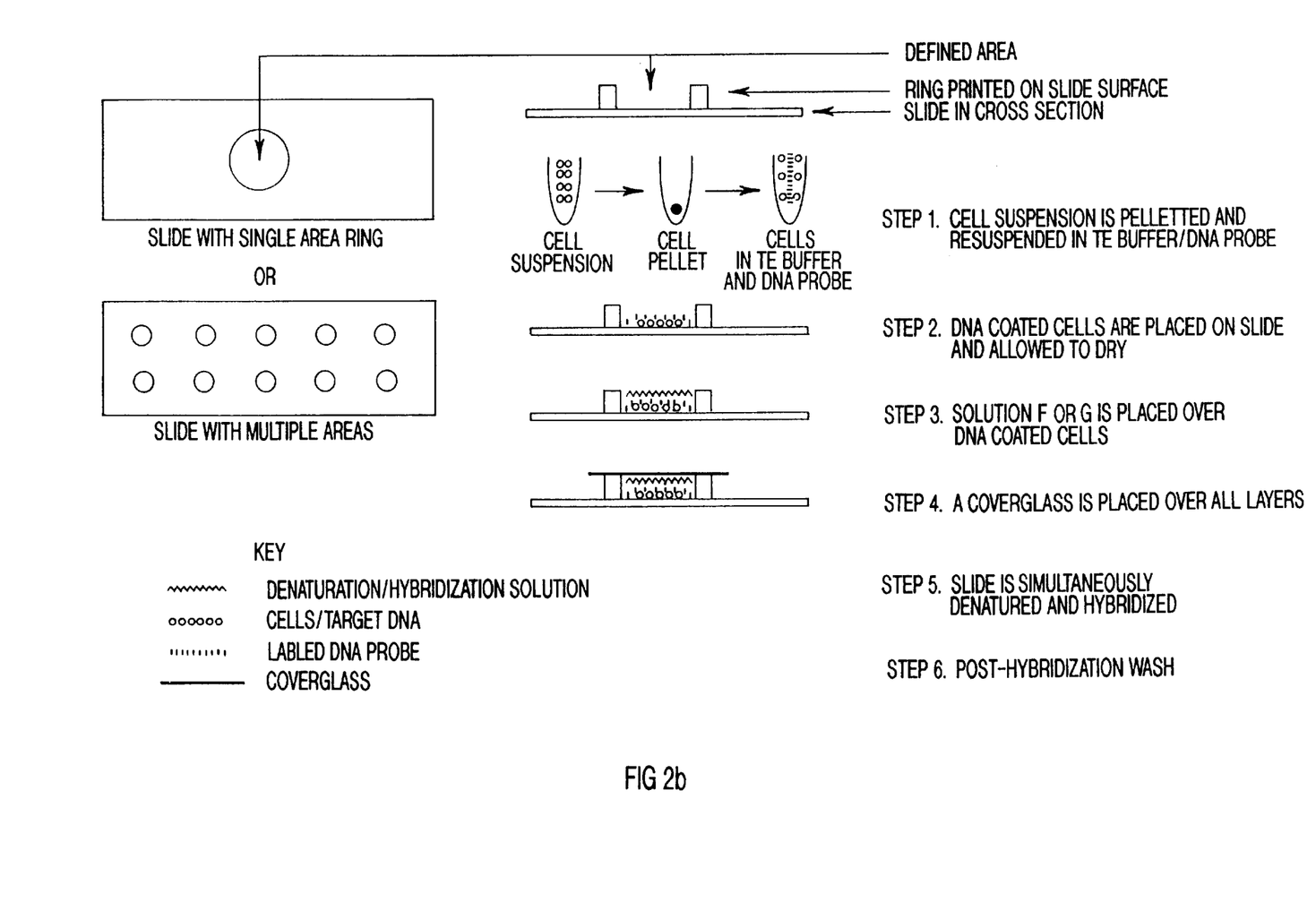
FIG. 2B illustrates a third embodiment of the invention.

Solution F or G is layered on top of the DNA probe coated cells. A coverglass is applied and the sample is simultaneously denatured and hybridized. This embodiment of the invention is shown in FIG. 2B.

Slide Method 3—Non-denatured Probe

With this embodiment, the DNA probe is not denatured. This is of particular importance when working with unique sequence, short segment, oligonucleotide probes (DNA), e.g., Vysis, Inc., LSI probes.

Figure 3:
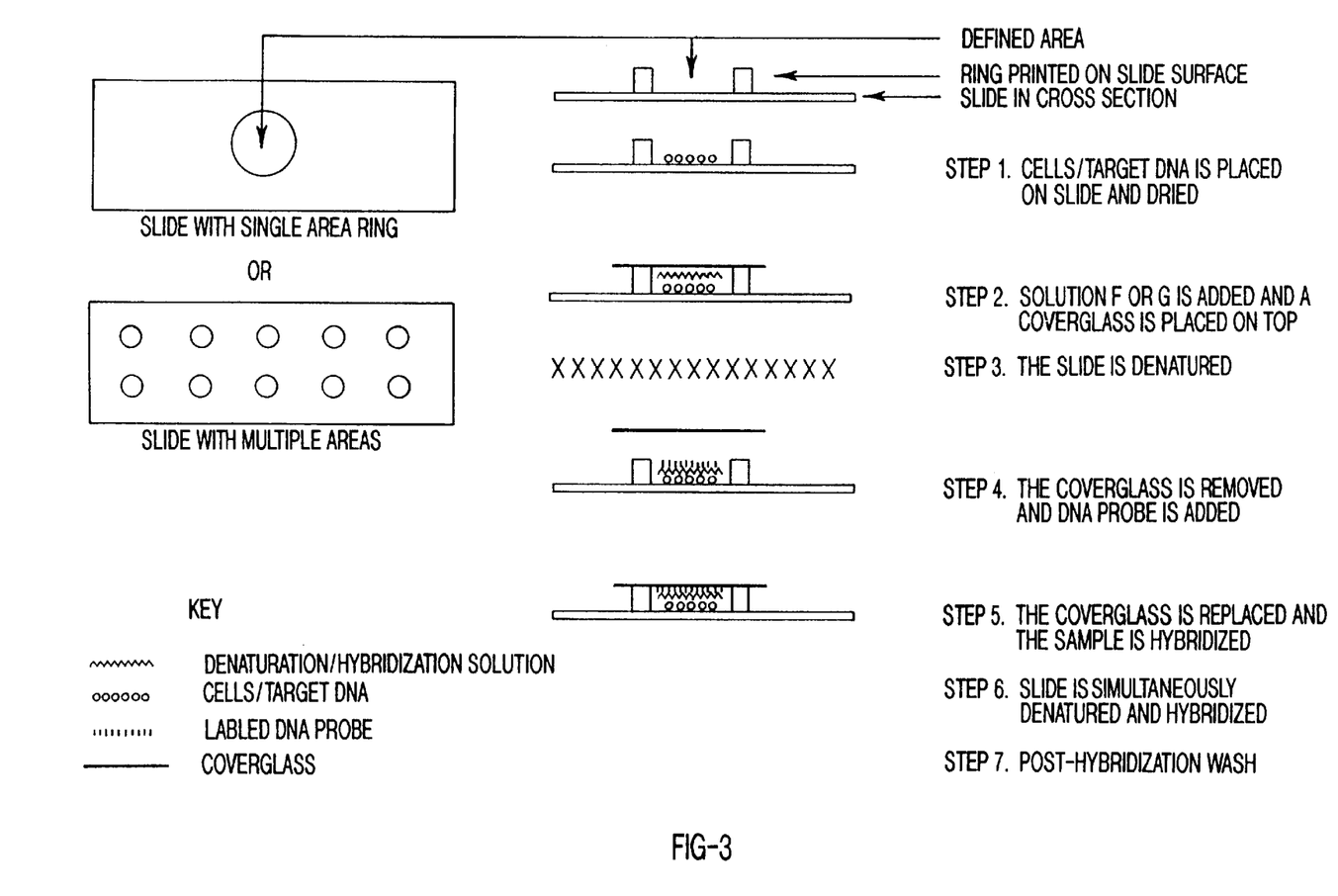
FIG. 3 illustrates a fourth embodiment of the invention.

Glass slides with defined area(s), e.g., ring(s), are used. The cell sample solution is applied to the slide within a defined area and allowed to dry. Solution F or G (for example) is layered on top of the cell sample. A coverglass is applied. The slide with the coverglassed sample is denatured at appropriate temperatures and times (see U.S. patent application Ser. No. 08/418,704). The coverglass is pushed to the side and DNA probe in TE buffer or other buffer is added, the coverglass is reapplied and sample hybridized. FIG. 3 illustrates this embodiment of the invention.

With the slide methods described above, after hybridization, the coverglass is removed, and a two-step post-hybridization wash is performed. First, the sample is placed in solution of 0.1% to 1% NP-40(noniodet P-40) in a 0.15% NaCl for thirty seconds to two minutes at 65° C. and, second, the sample is placed in a solution of 0.15% NaCl for three minutes to ten minutes at 65° C.

The above description of the present invention defines the optimal conditions under which the whole FISH process can be completed. Other conditions may be used, for example, any temperature for denaturation and hybridization can be used, as long as the temperature does not exceed approximately 110° C. These other conditions for FISH are described in U.S. patent application Ser. No. 08/418,704.

Industrial Applicability

The invention is further illustrated by the following non-limiting examples.

EXAMPLE 1

FISH performed with F and G solutions on various cell and tissue samples with simultaneous denaturation/hybridization of sample and probes.

1) Materials

A mixed probe of Rhodamine-labeled specific DNA for X chromosome and FITC (fluorescent isothiocyanate)-labeled specific DNA for Y chromosome probes (or Rhodamine-labeled Y chromosome and FITC-labeled X chromosome DNA probes) were obtained from a commercial source (Oncor, Inc., Vysis, Inc., BDS/Amersham, Inc.). The probes were diluted with various denaturation-hybridization solution F and G. (see U.S. patent application Ser. No. 08/418,704).

2) Preparation of Cell and Tissue Samples a) Leukocytes were obtained from peripheral blood as follows: Freshly collected blood from donors were subjected to routine Histopaque centrifugation. Mononuclear and granulocyte cells were combined and washed once with PBS (phosphate buffered saline). The washed cell pellets were treated with cold methanol/acetic acid (3:1), and kept at −20° C. until use for FISH.

b) Metaphase spreads or interphase cells of cultured and uncultured peripheral lymphocytes were immobilized on the glass slides according to standard cytogenetic procedures; methanol/acetic acid treated cells were placed on glass slides. Slides were air dried.

c) 5% paraformaldehyde-treated cells were treated with cold methanol/acetic acid (3:1), and kept at −20° C. for at least 30 minutes. Then, the methanol/acetic treated cells were applied on glass slides. When the slides were dried, proteinase K (50 $\mu$g/ml) was applied to each cell smear, and the slides were and incubated for 10 minutes at 38° C. Then the slides were washed with 0.05M Tris buffer, pH 7.4, and then air dried.

d) Paraformaldehyde-fixed, paraffin-embedded tissue sections were deparaffinized according to the standard procedures (with xylene and graded alcohols). The deparaffinized sections were treated with proteinase K as described above. The slides were air dried.

3) Preparation of Denaturation-hybridization Solutions: Solutions F and G a) Solution F: See U.S. patent application Ser. No. 08/418,704.

b) Solution G: See U.S. patent application Ser. No. 08/418,704.

4) Simultaneous Denaturation/hybridization of Samples and Probes

In this invention, "labeled probes" represent DNA or anti-sense RNA to which relatively heat-stable enzymes and ligands, fluorochromes, (e.g., FITC, rhodamine, Texas Red) chromophores, chemiluminescers, bioluminescers, or radioisotopes were covalently conjugated. The labeled probes were diluted with solution F or G or TE buffer to an appropriate concentration. Thus, the "probe solution" represents labeled probes.

In slide method 1 (see FIG. 1) (DNA-coated slides), 5 to 30 ul of diluted probe solution is placed on the slide and allowed to dry. The cell sample is placed on top of the DNA probe and allowed to dry. Solution F or G is layered over the cells/DNA probe area and covered with a coverglass.

In slide method 2A (see FIG. 2A) (DNA-coated cells), 5 to 30 μl of the diluted probe solution was spotted on nuclei, or an appropriately treated cells or tissue sections on the glass slides and allowed to dry. Solution F or G is layered on top and a coverglass was gently applied to cover the solution.

In slide method 2B (see FIG. 2B), the diluted probe solution is added to the pellet of cells in which the supernatant fixative has been decanted. The cells are resuspended and applied to the slide and allowed to dry. Solution F or G is layered on top of the DNA-covered slide.

Figure 4:
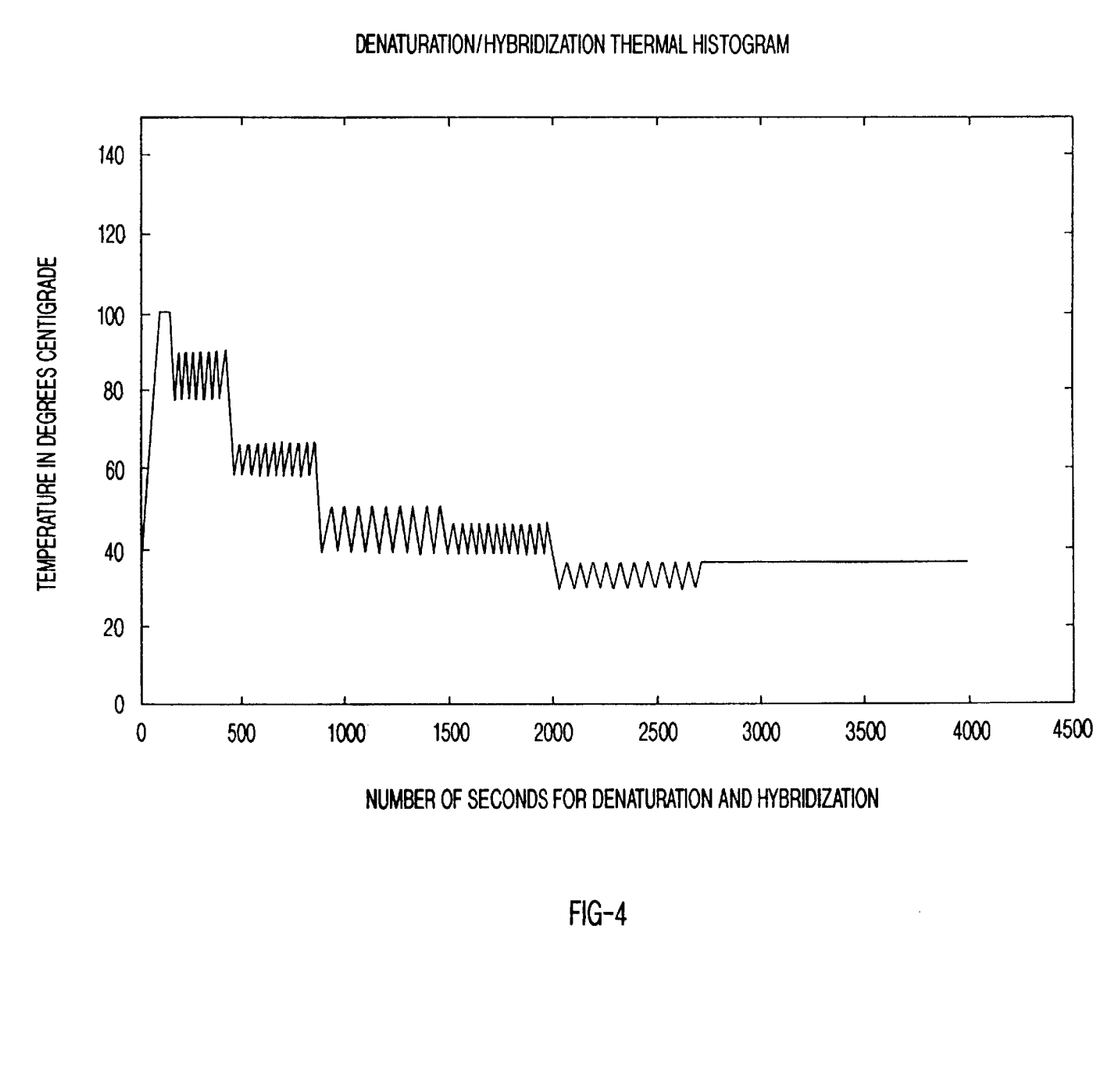
FIGS. 4–6 graphically illustrate temperature cycling according to the invention.
Figure 5:
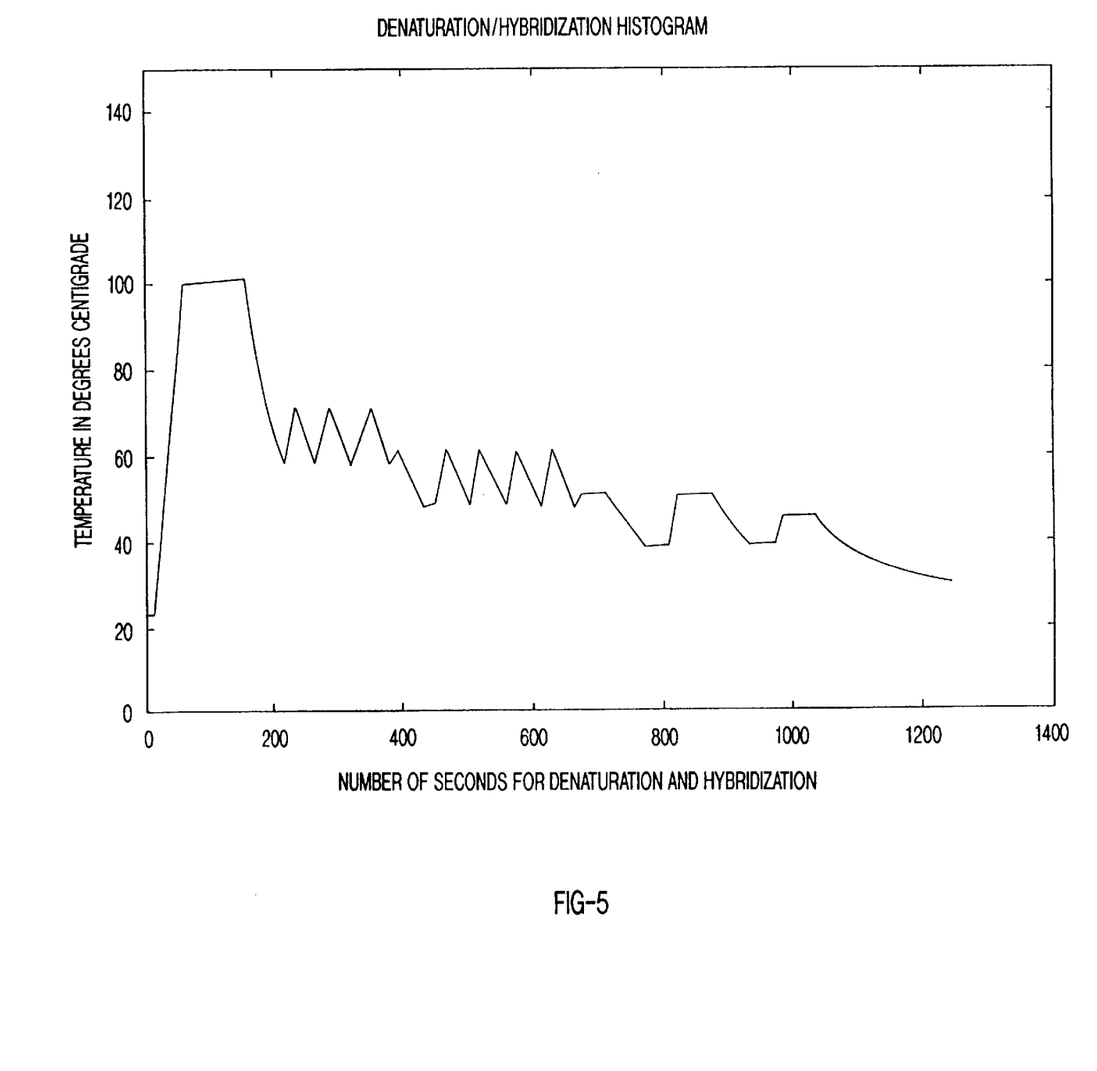
Figure 6:
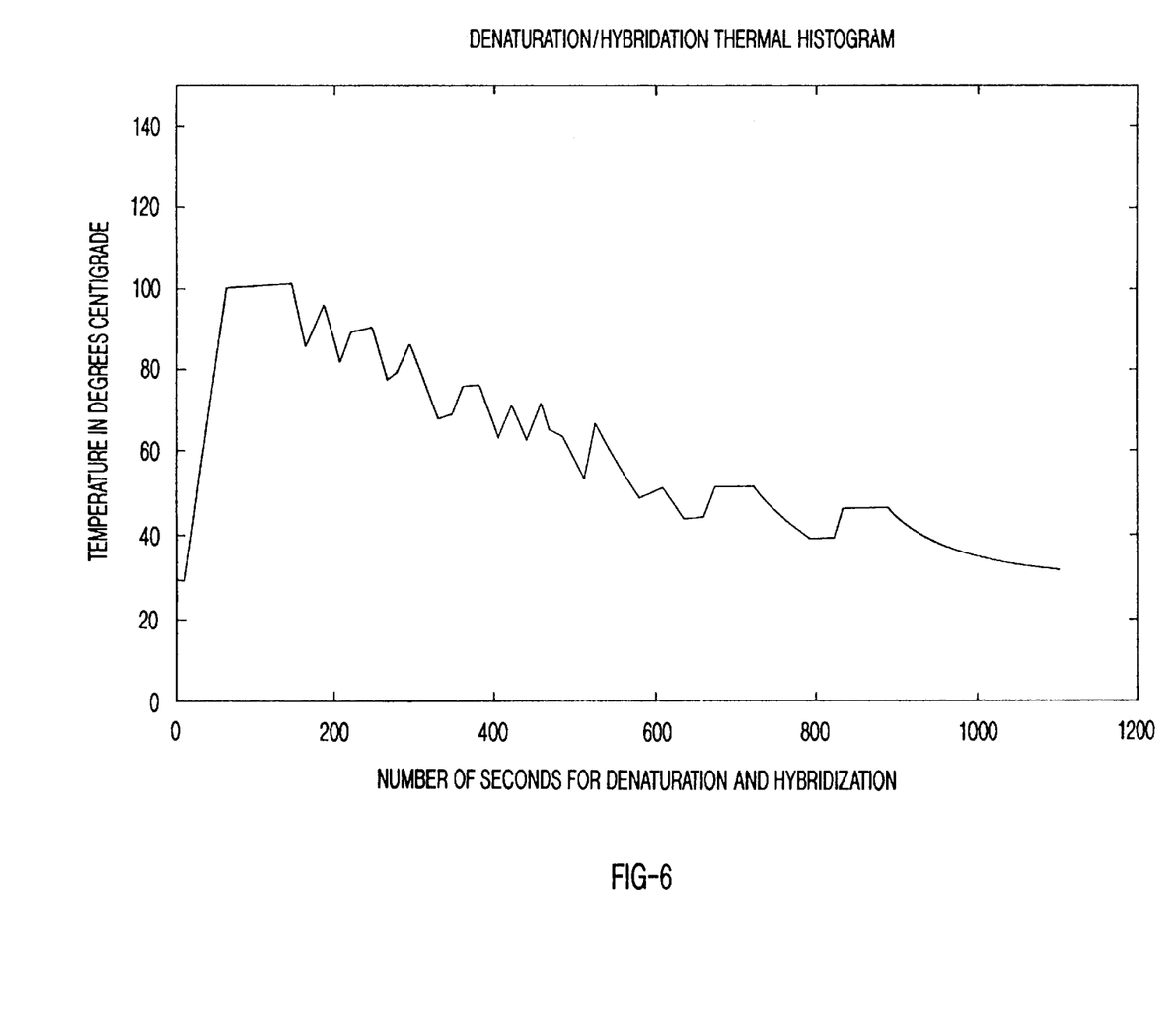

The slides are placed in a thermal cycler where the DNA is denatured for about 1½ minutes at 100° C. and then hybridized by rapidly reducing the temperature and cycling the temperature for about one minute to one hour. FIGS. 4–6 illustrate example cyclings.

The temperature and time for denaturation/hybridization can vary as described in U.S. patent application Ser. No. 08/418,704.

5) Post-hybridization Washings

After hybridization, the coverslips were removed from glass slides and the slides were immersed in 0.1% to 1% NP-40 for thirty seconds to two minutes and 0.1%–0.2% NaCl solution for three minutes.

6) Visualization of Fluorescence in situ Hybridization Signals

After post-hybridization washings, a small amount of counterstain (200 ng/ml of propidium iodide (PI) or 20 ng/ml of 4,6-diamidino-2-phenylindole (DAPI) in antifade) was spotted on the slide to counterstain nuclei. Hybridization signals in the nuclei were viewed using an Olympus inverted fluorescence microscope.

EXAMPLE 2

Slide Technology 3 (Non-denatured Probe)

In this example, a unique sequence, short segment, oligonucleotide probe(DNA) were used on cultured and uncultured, male, peripheral blood leukocytes. The purpose was to perform FISH procedures.

1) Materials and preparation of cell and tissue sample and preparation of denaturation/hybridization Solutions F and G were prepared as set forth in Example 1.

2) The cell sample solution is applied to the slide and allowed to dry. Solution F or G is layered on top of the cell sample and covered with a coverglass.

The sample is denatured at 100° C. for 1½ minutes in the thermal cycler. The thermal cycler is paused and the slide removed. The coverglass is pushed to the side, and the DNA probe in TE buffer is added. The coverglass is reapplied and the sample placed in the thermal cycler and cycle-hybridized.

The temperature and time for denaturation and hybridization can vary as described in U.S. patent application Ser. No. 08/418,704.

3) Post-hybridization wash is carried out as set forth in Example 1.

EXAMPLE 3

DNA FISH in fixed paraffin-embedded tissue sections using direct-labeled fluorescent and indirect-labeled DNA probes.

In this example, paraffin-embedded tissue sections were deparaffinized and dehydrated. (See U.S. patent application Ser. No. 08/418,704.)

For FISH the tissue sections (target DNA) were treated as set forth in Example 1, slide method 2A.

EXAMPLE 4

DNA FISH in Peripheral blood mononuclear cells (PBMC) and polymorphonuclear cells (PMN) using different fixatives and direct-labeled fluorescent and indirect-labeled DNA probes In this example, different fixatives were used with the direct-labeled fluorescent and indirect-labeled DNA probes. The purpose was to demonstrate the versatility of the present invention with various fixatives. Peripheral blood was collected in an anticoagulant tube and the PBMN and PNM separated as described in prior art and fixed in several fixatives: 1) 3:1 Methanol:Glacial acetic acid (MeOH:Hac) fixative for a minimum of 30 minutes at −20° C.; 2) 4% paraformaldehyde for 30 minutes to 3 hours and then applied to slides which were air dried for processing; and 3) Methanol for 30 minutes minimum at −20° C.

Methods of Fixation were as Follows (1) The 3:1 MeOH:Hac fixation method is previously described in Example 1.

(2) In the paraformaldehyde fixation method, the paraformaldehyde-fixed cells on air dried slides were treated with proteinase K at 2.5 ug/ml to 10 ug/ml and digested for 30 minutes to 1½ hours at 37° C. and washed 3 times in PBS.

(3) In the methanol fixation method, the sample cells were vortexed at high speed, and −20° C. methanol was added a few drops at a time to a total of 8 ml; the samples were then placed in a −20° C. freezer for a minimum of 30 minutes.

Following each fixative method described above, the samples were processed by the optimal methods previously described herein (see Example 1). The slides were viewed with a Texas red triple bandpass filter on a fluorescent microscope; signals were observed with a 40× dry objective lens in the interphase nuclei.

EXAMPLE 5

FISH in fetal cells from the maternal peripheral blood circulation fixed in 3:1 MeOH/Hac using direct-labeled fluorescent and indirect-labeled DNA probes Maternal peripheral blood was collected in an anticoagulant tube and the fetal cells separated as described in prior art and fixed in 3:1 MeOH:Hac fixative for a minimum of 30 minutes at −20° C. The samples were centrifuged at 1000 g's for 10 minutes, and 10 ul of sample applied to each slide until a density of cells was reached sufficient for analysis.

The samples were processed by previously described optimal methods (Example 1, 2 and 3). The slide was viewed with a Texas red triple bandpass filter on an epifluorescent microscope.

EXAMPLE 6

FISH in sperm and non-cultured amniocytes fixed in 3:1 MeOH/Hac using direct-labeled fluorescent and indirect-labeled DNA probes The preparation of sperm and non-cultured amniocytes for FISH was identical. Aliquots of sperm or amniocytes were placed into 15 ml centrifuge tubes. PBS-containing 2 mM Dithiothreitol (DTT) was added to sperm or amniocytes at a concentration of 10 to $20 \times 10_6$ per ml for 6.5 minutes at room temperature to decondense the chromatin. The sample-containing tubes were then centrifuged at 160 g's for 5 minutes. Supernatant was discarded, 8 ml of −20° C. 3:1 MeOH/Hac were added, and the sample was vortexed. The samples were then fixed at −20° C. 3:1 MeOH:Hac for a minimum of 30 minutes. Preferable fixation time is overnight at −20° C. After this fixation, the sperm or amniocyte samples were centrifuged at 1000 g's for 10 minutes. The supernatant was removed, samples were resuspended in an appropriate volume of 3:1 MeOH:Hac, and 10 ul of sample suspended in fixatives were placed on each slide (in a 12 mm circle) assuring an even distribution. The slides were air dried for a minimum of 5 minutes.

The samples were processed by the previously described preferred method (see Example 1), then viewed and counted using a fluorescence microscope with a Texas red triple band pass filter on a 60× dry objective lens.

The preceding examples can be repeated with similar success by substituting the generically or specifically described reactants and/or operating conditions of this invention for those used in the preceding examples. Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, are hereby incorporated by reference. As disclosed in the parent patent application, an additional condition may include the use of a hot aluminum shelf containing the denatured slides for hybridization.

What is claimed is:

1. A method of preparing a fluorescent in situ hybridization slide, the method comprising the steps of:
    a) adding a slide;
    b) adding to the slide a nucleic acid probe;
    c) adding to the slide a target nucleic acid;
    d) adding to the slide a hybridization solution;
    e) after step (b), drying the slide to remove moisture;
    f) denaturing contents of the slide;
    g) hybridizing contents of the slide; and
    h) performing a post-hybridization wash of the slide.

2. The method of claim 1 wherein the step of adding a nucleic acid probe comprises coating the slide with the probe to form a first layer, the step of adding a target nucleic acid comprises layering the target nucleic acid on top of the probe coating to form a second layer, and the step of adding a solution comprises layering the solution on top of the first layer of probe coating and the second layer of target nucleic acid.

3. The method of claim 1 wherein step (c) is performed before step (b) and comprises applying the target nucleic acid to the slide to form a layer, step (b) comprises adding to the target nucleic acid a coating with the probe to concentrate the nucleic acid probe on the target nucleic acid, and the step (d) of adding a solution comprises layering the solution on top of the probe-coated target nucleic acid.

4. The method of claim 1 wherein:
    step (c) is performed simultaneously with step (b) and the method further comprises a step performed prior to step (c) of adding a target nucleic acid in solution, centrifuging the solution containing the target nucleic acid to pellet the target nucleic acid, and decanting such solution;
    step (b) comprises applying the nucleic acid probe to the pelleted target nucleic acid to form a coating, resuspending the probe-coated target nucleic acid in a resuspension solution, and applying the resuspension solution to the slide to form a first layer; and
    the step of providing a hybridization solution comprises layering the hybridization solution on top of the probe-coated target nucleic acid to form a second layer.

5. The method of claim 1 wherein:
    step (c) is performed before step (b) and further comprises adding a target nucleic acid in solution to the slide and allowing the applied target nucleic acid to dry on the slide;
    step (d) is performed before step (b) and further comprises applying the solution as a layer on top of the target nucleic acid on the slide;
    step (e) is performed after step (c);
    step (f) is performed after step (e); and
    step (b) is performed after step (f).

6. The method of claim 1 wherein the step of adding a solution comprises providing a solution selected from the group of hybridization solutions consisting of: a formamide-free mixture comprising 10%±2% by weight dextran sulfate, 15%–25% by weight glycerol, and 0.9% by weight salt; and a mixture comprising 10%±2% by weight dextran sulfate, 10%–30% by volume formamide, and 0.9% by weight salt.

7. The method of claim 6 wherein the solution further comprises diethylpyrocarbonate.

8. The method of claim 1, wherein steps (f) through (g) are performed in two minutes or less.

9. The method of claim 1, wherein the step of adding a probe further comprises diluting the probe before application.

10. The method of claim 9, wherein the step of diluting the probe comprises diluting the probe with buffer.

11. The method of claim 10, wherein the buffer comprises Tris-EDTA buffer.

12. The method of claim 6, wherein the salt is selected from the group consisting of NaCl, KCl and a mixture of sodium chloride and citric acid trisodium (SSC).

13. The method of claim 1, wherein the steps of denaturation and hybridization of combined probe and target contents of the slide are performed sequentially.

14. The method of claim 1, wherein the steps of denaturation and hybridization are conducted in 5 minutes or less.

15. The method of claim 1, wherein the step of denaturation is conducted in 1 to 2 minutes.

16. The method of claim 15, wherein the step of denaturation is conducted at a temperature between about 95° C. and 105° C.

17. The method of claim 1, wherein the step of performing a post-hybridization wash is conducted in 5 to 10 minutes.

18. The method of claim 17, wherein the step of performing a post-hybridization wash is conducted at between about 55° C. and 65° C.

19. The method of claim 1, wherein the step of performing a post-hybridization wash comprises the steps of:
   washing the slide in a first solution comprising a salt; and
   washing the slide in a second solution comprising a salt.

20. The method of claim 19, wherein the first solution comprising a salt comprises NaCl and a detergent.

21. The method of claim 20, wherein the first solution comprising a salt comprises 0.15% NaCl and 0.1–1% detergent.

22. The method of claim 19, wherein the step of washing in the first solution is performed for 30 seconds to 2 minutes.

23. The method of claim 22, wherein the step of washing in the first solution is performed at a temperature of 65° C.

24. The method of claim 19, wherein the second solution comprises NaCl.

25. The method of claim 24, wherein the second solution comprises 0.1–0.2% NaCl.

26. The method of claim 19, wherein the step of washing in a second solution is performed for about 3–10 minutes.

27. The method of claim 26, wherein the step of washing in the second solution is performed at a temperature of about 65° C.

28. The method of claim 1, wherein the step of denaturation is conducted in a thermal cycler for about 1.5 minutes at about 100° C.

29. The method of claim 1, wherein the step of hybridization is conducted in a thermal cycler and comprises the step of reducing temperature in a manner such that temperature fluctuates in amplitude and frequency about a descending temperature gradient until hybridization has occurred to a predetermined desired level.

30. The method of claim 29, wherein the step of reducing temperature is conducted for about 1 minute to 1 hour.

31. The method of claim 1, wherein the steps of denaturation and hybridization are conducted at a temperature not exceeding about 110° C.

32. The method of claim 1 wherein the steps of denaturation and hybridization occur in the absence of a step of providing a fixative to the contents of the slide.

33. The method of claim 1 wherein the step of performing a post-hybridization wash comprises washing in the absence of formamide.

34. The method of claim 1 wherein the step of hybridization is conducted under a controlled descent from a denaturation temperature to ambient room temperature.

35. A method of preparing a fluorescent in situ hybridization slide, the method comprising the steps of:
   a) providing a slide;
   b) adding to the slide a nucleic acid probe;
   c) adding to the slide a target nucleic acid;
   d) adding to the slide a hybridization solution;
   e) after step (b), drying the slide to remove moisture;
   f) denaturing contents of the slide at a temperature of between 95° C.–105° C.;
   g) hybridizing contents of the slide at a temperature of between 45° C.–60° C.; and
   h) performing a post-hybridization wash of the slide, wherein denaturization, hybridization and post-hybridization are all completed within 15 minutes.

36. The method of claim 35 wherein the step of adding a solution comprises providing a solution selected from the group of hybridization solutions consisting of: a formamide-free mixture comprising 10%±2% by weight dextran sulfate, 15%–25% by weight glycerol, and 0.9% by weight salt; and a mixture comprising 10%±2% by weight dextran sulfate, 10%–30% by volume formamide, and 0.9% by weight salt.

37. The method of claim 36 wherein the step of adding a solution additionally comprises providing diethylpyrocarbonate.

38. The method of claim 36, wherein the salt is selected from the group consisting of NaCl, KCl and a mixture of sodium chloride and citric acid trisodium (SSC).

39. The method of claim 35 wherein the steps of denaturation and hybridization occur in the absence of a step of providing a fixative to the contents of the slide.

40. The method of claim 35 wherein the step of post-hybridization comprises washing in the absence of formamide.

41. A method of preparing a fluorescent in situ hybridization slide for mRNA, the method comprising the steps of:
   a) providing a slide;
   b) adding to the slide a nucleic acid probe;
   c) adding to the slide a target nucleic acid;
   d) adding to the slide a hybridization solution;
   e) after step (b), drying the slide to remove moisture;
   f) prehybridizing contents of the slide at a temperature of between 37° C.–55° C.;
   g) denaturing contents of the slide at a temperature of between 95° C.–105° C.;
   h) hybridizing contents of the slide in 5 minutes or less at a temperature of between 45° C.–85° C.; and
   i) performing a post-hybridization wash of the slide, wherein denaturation, hybridization and post-hybridization are all completed within 15 minutes.

42. A method of preparing a fluorescent in situ hybridization slide for mRNA target or probe, the method comprising the steps of:
   a) providing a slide;
   b) adding to the slide a nucleic acid probe;
   c) adding to the slide a target nucleic acid;
   d) adding to the slide a hybridization solution;
   e) after step (b), drying the slide to remove moisture;
   f) performing prehybridization;
   g) performing hybridization in 5 minutes or less; and
   h) performing post-hybridization; wherein the steps of performing prehybridization, hybridization and post-hybridization are completed within 24 hours.

43. A method of preparing a fluorescent in situ hybridization slide for mRNA target or probe, the method comprising the steps of:
   a) providing a slide;
   b) adding to the slide a nucleic acid probe;
   c) adding to the slide a target nucleic acid;
   d) adding to the slide a hybridization solution;
   e) after step (b), drying the slide to remove moisture;
   f) performing prehybridization at a temperature of between 37° C. and 55° C.;
   g) performing hybridization in 5 minutes or less at a temperature of between 45° C. and 85° C.; and
   h) performing post-hybridization; wherein the steps of performing prehybridization, hybridization and post-hybridization are completed within 24 hours.

44. The method of claim 1 wherein the step of providing a slide comprises providing a slide comprising a raised ring thereon.

45. The method of claim 35 wherein the step of providing a slide comprises providing a slide comprising a raised ring thereon.

46. A method of preparing a fluorescent in situ hybridization slide, the method comprising the steps of:
   a) providing a slide;
   b) adding to the slide a nucleic acid probe;
   c) adding to the slide a target nucleic acid;
   d) adding to the slide a hybridization solution;
   e) denaturing contents of the slide; and
   f) hybridizing contents of the slide, comprising reducing temperature in a manner such that temperature fluctuates in amplitude and frequency about a descending temperature gradient until hybridization has occurred to a predetermined desired level.

47. The method of claim 46 additionally comprising, after a step selected from the group consisting of steps (b) and (c), drying the slide to remove moisture.

48. A method of preparing a fluorescent in situ hybridization slide, the method comprising the steps of:
   a) providing a slide;
   b) adding to the slide a nucleic acid probe;
   c) adding to the slide a target nucleic acid;
   d) adding to the slide a hybridization solution;
   e) denaturing contents of the slide; and
   f) hybridizing contents of the slide conducted under a descent from a denaturation temperature to ambient room temperature.

49. The method of claim 48 additionally comprising, after a step selected from the group consisting of steps (b) and (c), drying the slide to remove moisture.

50. The method of claim 48 wherein the hybridization step is conducted under a controlled descent from a denaturation temperature to ambient room temperature.

51. The method of claim 1 wherein steps (f) and (g) are conducted simultaneously.

52. A method of preparing a fluorescent in situ hybridization slide, the method comprising the steps of:
   a) providing a slide;
   b) adding to the slide a nucleic acid probe;
   c) adding to the slide a target nucleic acid;
   d) adding to the slide a hybridization solution;
   e) denaturing contents of the slide; and
   f) hybridizing contents of the slide under a controlled descent from a denaturation temperature to ambient room temperature; and
   wherein at least one step selected from the group of steps consisting of (e) and (f) is performed on a shelf.

53. The method of claim 52 wherein the shelf is heat-conductive.

54. The method of claim 53 wherein the shelf is a plate.

55. The method of claim 54 wherein the plate comprises aluminum.

* * * * *

UNITED STATES PATENT AND TRADEMARK OFFICE
CERTIFICATE OF CORRECTION

PATENT NO. : 6,022,689
DATED : February 8, 2000
INVENTOR(S) : Sarto et al.

It is certified that error appears in the above-identified patent and that said Letters Patent is hereby corrected as shown below:

Title page,
Item [54], Title, before the word "SITU" please insert the word -- IN --.

Signed and Sealed this

Fourth Day of January, 2005

JON W. DUDAS
*Director of the United States Patent and Trademark Office*

UNITED STATES PATENT AND TRADEMARK OFFICE
CERTIFICATE OF CORRECTION

PATENT NO. : 6,022,689
DATED : February 8, 2000
INVENTOR(S) : Sarto et al.

Page 1 of 1

It is certified that error appears in the above-identified patent and that said Letters Patent is hereby corrected as shown below:

Title page,
Item [54], Title, before the word "SITU" please insert the word -- IN --.
Item [56], References Cited, U.S. PATENT DOCUMENTS, please insert the following:
-- 3,883,398    05/1975    Ono
  5,538,872    07/1996    Bahl et al.
  5,554,500    09/1996    Brann et al.
  5,571,721    11/1996    Turner
  5,576,178    11/1996    Emanuel et al. --

Signed and Sealed this

Nineteenth Day of April, 2005

JON W. DUDAS
*Director of the United States Patent and Trademark Office*